US009149848B2

(12) United States Patent
Grzyb et al.

(10) Patent No.: US 9,149,848 B2
(45) Date of Patent: Oct. 6, 2015

(54) METHOD AND APPARATUS FOR TRIMMING A SAMPLE FROM A COILED METAL WEB

(75) Inventors: Jennifer Grzyb, McMurray, PA (US); Patrick Salpeck, Baden, PA (US); Len Walnoha, McMurray, PA (US)

(73) Assignee: Primetals Technologies USA LLC, Alpharetta, GA (US)

( * ) Notice: Subject to any disclaimer, the term of this patent is extended or adjusted under 35 U.S.C. 154(b) by 644 days.

(21) Appl. No.: 13/333,845

(22) Filed: Dec. 21, 2011

(65) Prior Publication Data

US 2012/0187091 A1    Jul. 26, 2012

Related U.S. Application Data

(60) Provisional application No. 61/434,630, filed on Jan. 20, 2011, provisional application No. 61/488,874, filed on May 23, 2011.

(51) Int. Cl.
| | | |
|---|---|---|
| *B23Q 5/00* | (2006.01) | |
| *B23D 37/22* | (2006.01) | |
| *B26D 3/00* | (2006.01) | |
| *B21C 47/24* | (2006.01) | |

(Continued)

(52) U.S. Cl.
CPC ............... *B21C 47/24* (2013.01); *B21C 51/00* (2013.01); *G01N 1/04* (2013.01); *Y10T 83/0304* (2015.04); *Y10T 83/04* (2015.04); *Y10T 83/0448* (2015.04); *Y10T 83/6667* (2015.04); *Y10T 409/303808* (2015.01); *Y10T 409/306048* (2015.01); *Y10T 409/4035* (2015.01); *Y10T 409/400175* (2015.01)

(58) Field of Classification Search
CPC ............ B21C 47/24; B21C 51/00; G01N 1/04
USPC ............... 219/69.1, 121.39, 121.44; 409/132, 409/172, 244, 263; 83/13, 23, 733, 875
See application file for complete search history.

(56) References Cited

U.S. PATENT DOCUMENTS 5,095,920 A * 3/1992 Mattei ........................ 131/117

FOREIGN PATENT DOCUMENTS

| DE | 2815969 A1 | 10/1979 |
|---|---|---|
| DE | 29 24 379 Al | 1/1981 |
| DE | 4411905 A1 | 11/1994 |

(Continued)

OTHER PUBLICATIONS

Machine translation of DE4411905.*

(Continued)

*Primary Examiner* — Jianying Atkisson
(74) *Attorney, Agent, or Firm* — Gesmer Updegrove LLP

(57) ABSTRACT

Sample extraction or trimming from an end strip of an elongated formed metal that is coiled in layers within a tensioned metal coil resting on driven rollers. A cut channel is formed across the material width. In some embodiments the cut channel is formed between the rollers and by cutting at an angle relative to the coil outer surface. Coil weight and/or a coil tensioner mechanism inhibits coil relaxation along the cut channel by maintaining tension on wrapped layers against each other when the coil is unbanded for sample extraction. The coil is rotated so that the cut channel clears the rollers laterally. Material downstream the cut is then separated from the coil. After trimming and/or sample extraction the coil maintains rolled tautness for ease of rebanding.

17 Claims, 11 Drawing Sheets

(51) Int. Cl.
*B21C 51/00* (2006.01)
*G01N 1/04* (2006.01)

(56) References Cited

FOREIGN PATENT DOCUMENTS

| DE | 10 2007 017383 A1 | 8/2008 |
|---|---|---|
| EP | 0 044 923 A2 | 2/1982 |
| EP | 0497182 A1 | 8/1992 |
| EP | 1 888 284 B1 | 5/2009 |
| GB | 2068796 A | 8/1981 |
| JP | 08 267134 A | 10/1996 |
| JP | 09085315 A * | 3/1997 |
| WO | WO 2006111259 A1 | 10/2006 |
| WO | 2012 113631 A1 | 8/2012 |

OTHER PUBLICATIONS

PCT International Search Report mailed May 7, 2012 corresponding to PCT International Application No. PCT/US2012/021845 filed Jan. 19, 2012 (12 pages).

* cited by examiner

METHOD AND APPARATUS FOR TRIMMING A SAMPLE FROM A COILED METAL WEB

CLAIM TO PRIORITY

This application claims the benefit of two co-pending United States provisional patent applications, respectively entitled: "Automated Heavy Gauge Sampling Station", filed, Jan. 20, 2011, and assigned Ser. No. 61/434,630 and "Method and Apparatus for Trimming a Sample from a Coiled Metal Web", filed, May 23, 2011, and assigned Ser. No. 61/488,874; both of which are incorporated by reference herein.

BACKGROUND

1. Field

Embodiments of the present invention relate to trimming ends from a coil of coiled formed metal without distorting the material remaining on the coil and maintaining the coil layers tightly wrapped in taut tension for banding or rebanding. Coil ends are trimmed for obtaining test and inspection samples, as well as for trimming scrap tail ends.

2. Description of the Prior Art

A known system places a banded metal coil of tightly wrapped formed elongated sheet material (e.g., a sheet web) between spaced parallel rollers, removes bands that maintain coiled metal layers in a tightly wrapped, taut layer condition, and thereafter unwinds a portion of the coil end so that a desired length extends generally tangentially from the coil laterally clear from the rollers. The tangential end is selectively cut through the full material thickness normal to its surface by a shear. The sheared-off tangential end separates from the roll and drops into a collection container. A remnant stub projects generally tangentially from the roller in a relaxed uncoiled deformed state that inhibits tight re-rolling and banding of the sampled coil. The sheared edge remaining on the coil may have localized distortion and a relatively blunt edge generally along the coil's radial circumference that may hinder further rotational maneuvering of the coil on the rollers. The known sampling system is monitored and controlled by a human operator.

SUMMARY

Accordingly, embodiments of the present invention include the creation a coil trimming and sampling system that, in one aspect reduces and in yet another prevents deformation of the coil material dimensions during the trimming or sampling procedure, and facilitates rebanding of the coil in its taut, fully coiled state.

Another embodiment of the present invention includes a coil trimming and sampling system that facilitates a clean separation of the coil sample from the coil while minimizing localized coil material dimensional deformation along the separation edge.

An additional embodiment of the present invention includes a coil trimming and sampling system that facilitates passage of the separation edge remaining on the coil over the rollers as the coil is manipulated, including for re-strapping the coil in it tensioned wrapped state.

Another exemplary embodiment includes an automated trimming and sample extraction system and method that does not require human intervention between sampling steps.

These and other embodiments can be achieved by a system and method for trimming or extracting a sample from the end of a metal coil. Ends are trimmed and/or samples are extracted from an end strip of a tensioned metal coil that is resting on rollers. In one embodiment, a cut channel is formed between the rollers by cutting at an angle relative to the coil outer surface. Coil weight inhibits coil relaxation along the cut channel. The coil can be rotated so that the cut channel clears the rollers laterally and the scrap end or sample downstream the cut channel is separated off the coil.

In embodiments of the present invention, cut channel depth and angle may be selected so that the trimmed/sampled end's full material thickness is not penetrated. The uncut necked material thickness remaining at the depth of the cut channel formation is selected to allow a clean separation of the material. Angular cutting reduces deformation of the material along the edge remaining on the coil and reduces the force required to separate the strip downstream the cut channel. If the separation force is less than the material's tensile strength there is less likelihood that the edge will be deformed. After sample extraction the coil maintains rolled tautness for ease of rebanding.

Embodiments of the present invention include sampling systems for extracting a sample from an end strip of a coil having wrapped layers of coiled formed elongated metal. The system has a pair of generally parallel spaced drive rollers that are driven by a roller drive system coupled thereto, for selective rotation of a coil about a coil central axis that is oriented parallel to the rollers. A cutter is proximal the rollers for alignment with a circumference of a metal coil resting on the driven rollers. The cutter has a cutter drive mechanism for selectively advancing the cutter into the coil and selectively traversing the cutter along the coil circumference. A coil tensioner mechanism maintains tension on wrapped layers against each other in a metal coil resting on the rollers, in order to inhibit relaxation of the coiled layers.

Embodiments of the present invention additionally include a method for extracting a sample form an end strip of a coil having wrapped layers of coiled formed elongated metal with a sampling system. The method is performed by placing a banded coil, having a central axis, on a pair of generally parallel spaced driven rollers so that the coil central axis is oriented parallel to the driven rollers. Tension is maintained between wrapped layers in the coil against each other with a coil tensioner, so that the coil can be unbanded without disturbing the tensioned layers. The coil is rotated with the driven rollers so that a desired length of end strip is oriented downstream the cutter. The end strip material is cut by selectively advancing and traversing the cutter into the coil in any desired sequence. The end strip is then extracted from the coil.

Further features of embodiments of the present invention, and the advantages offered thereby, are explained in greater detail hereinafter with reference to specific embodiments illustrated in the accompanying drawings, wherein like elements are indicated by like reference designators.

BRIEF DESCRIPTION OF THE DRAWINGS

The teachings of the present invention can be readily understood by considering the following detailed description in conjunction with the accompanying drawings, in which.

To facilitate understanding, identical reference numerals have been used, where possible, to designate identical elements that are common to the figures.

DETAILED DESCRIPTION

After considering the following description, those skilled in the art will clearly realize that the teachings of my invention can be readily utilized in coiled metal sample extraction systems and methods.

General System Overview

Figure 1:
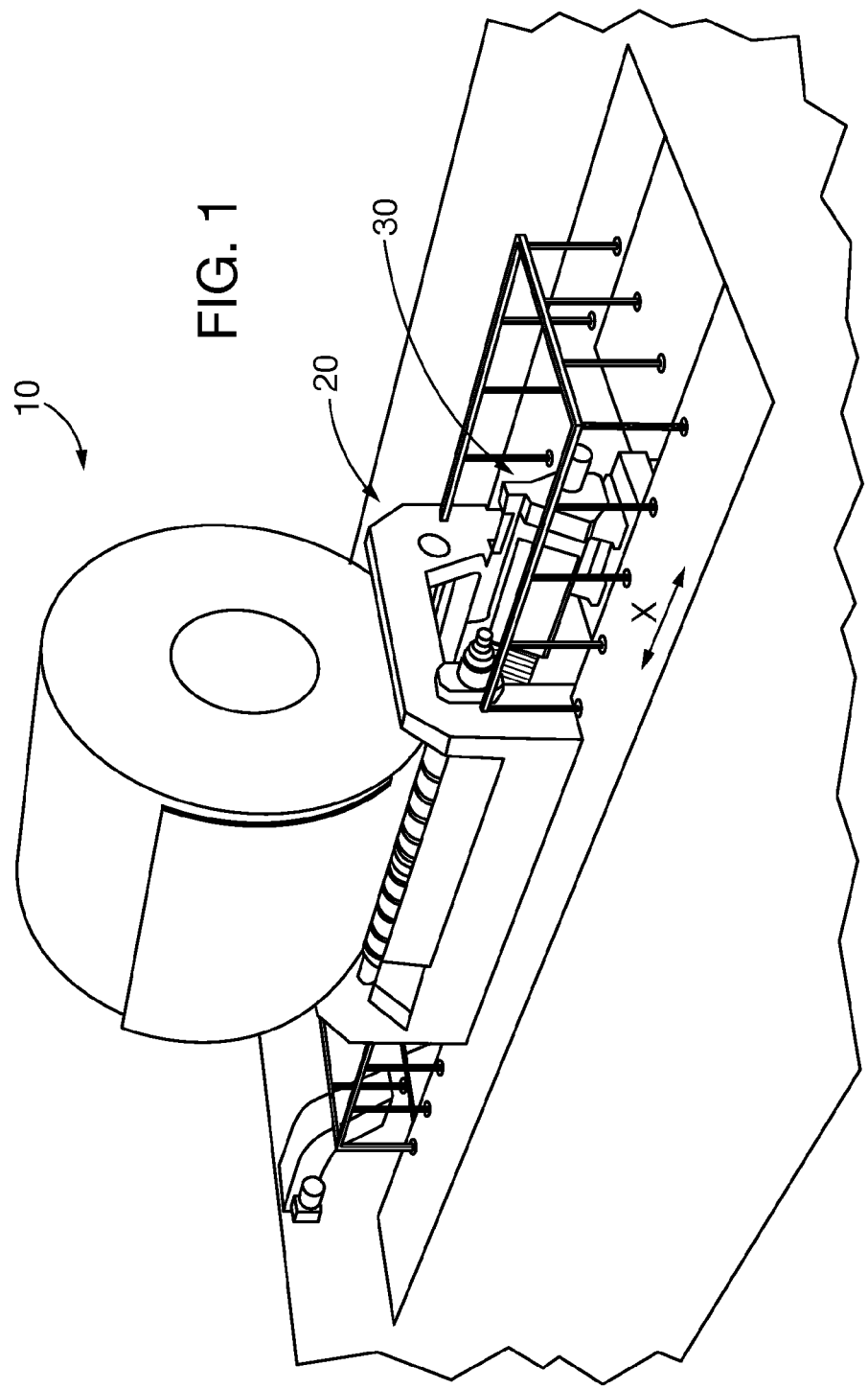
FIG. 1 is a perspective view of a system loaded with a metal coil, in accordance with an exemplary embodiment of the present invention.
Figure 2:
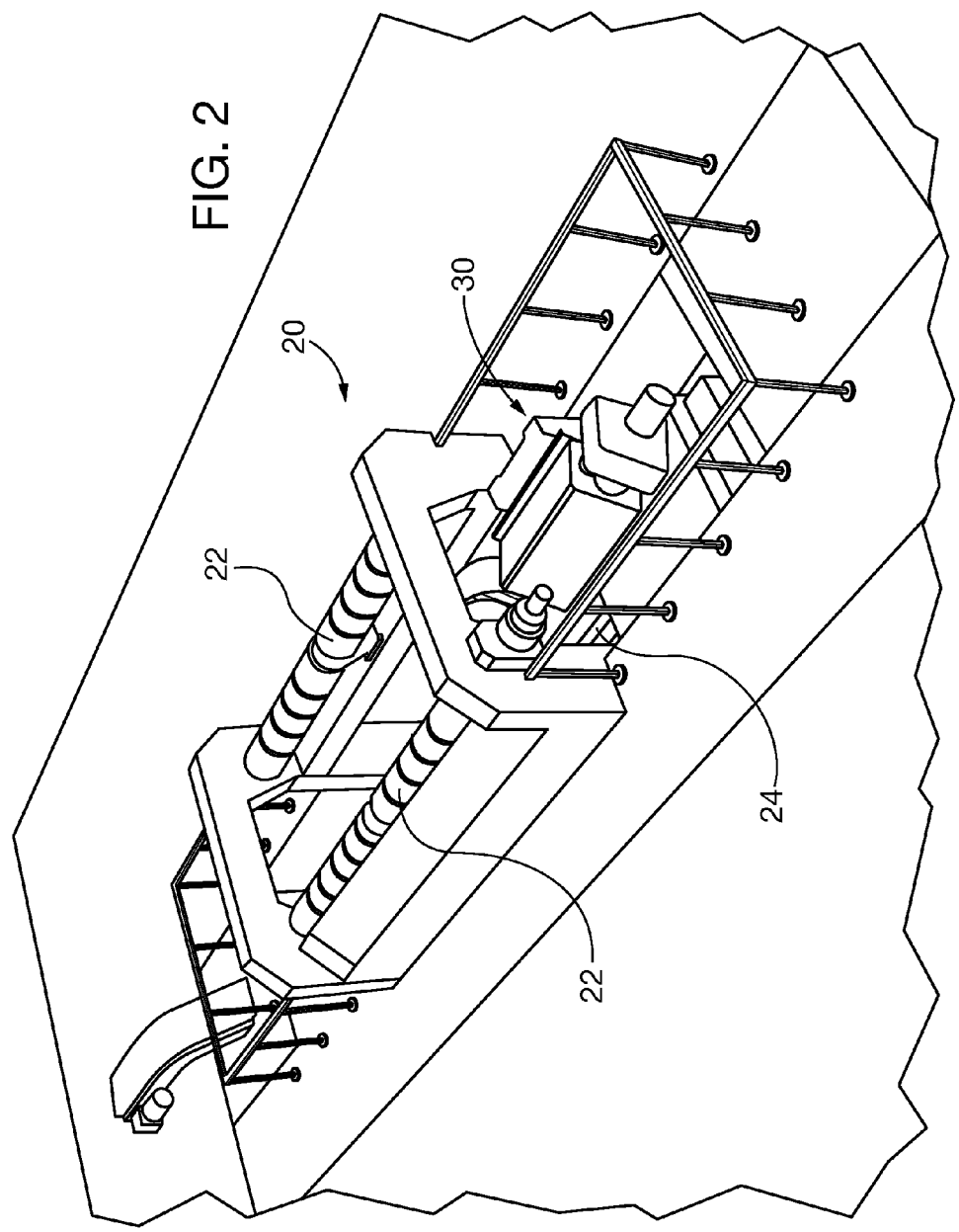
FIG. 2 is a perspective view of the system of FIG. 1 without a metal coil, in accordance with an exemplary embodiment of the present invention.

Referring generally to FIGS. 1 and 2, showing one exemplary embodiment of the present invention, a coiled metal web 10 is placed in a sample extraction system 20, where it rests on at least a pair of driven rollers 22, in an exemplary embodiment there are two driven rollers as illustrated in FIGS. 1 and 2, that are capable of causing rotation of the coil 10 about its central rotational axis. While coiled sheet web is shown in the figures herein, other types of elongated coiled formed metal may be accommodated in the sampling system of the present invention, including by way of nonlimiting example rebar, round or rectangular barstock, pipe and tubing. A sample cutter 30 can be positioned parallel to and between the rollers 22, as well as the coil 10 central rotational axis. The sample cutter 30 is driven by a linear drive 24 along the X axis transverse the coiled sheet web.

Figure 3:
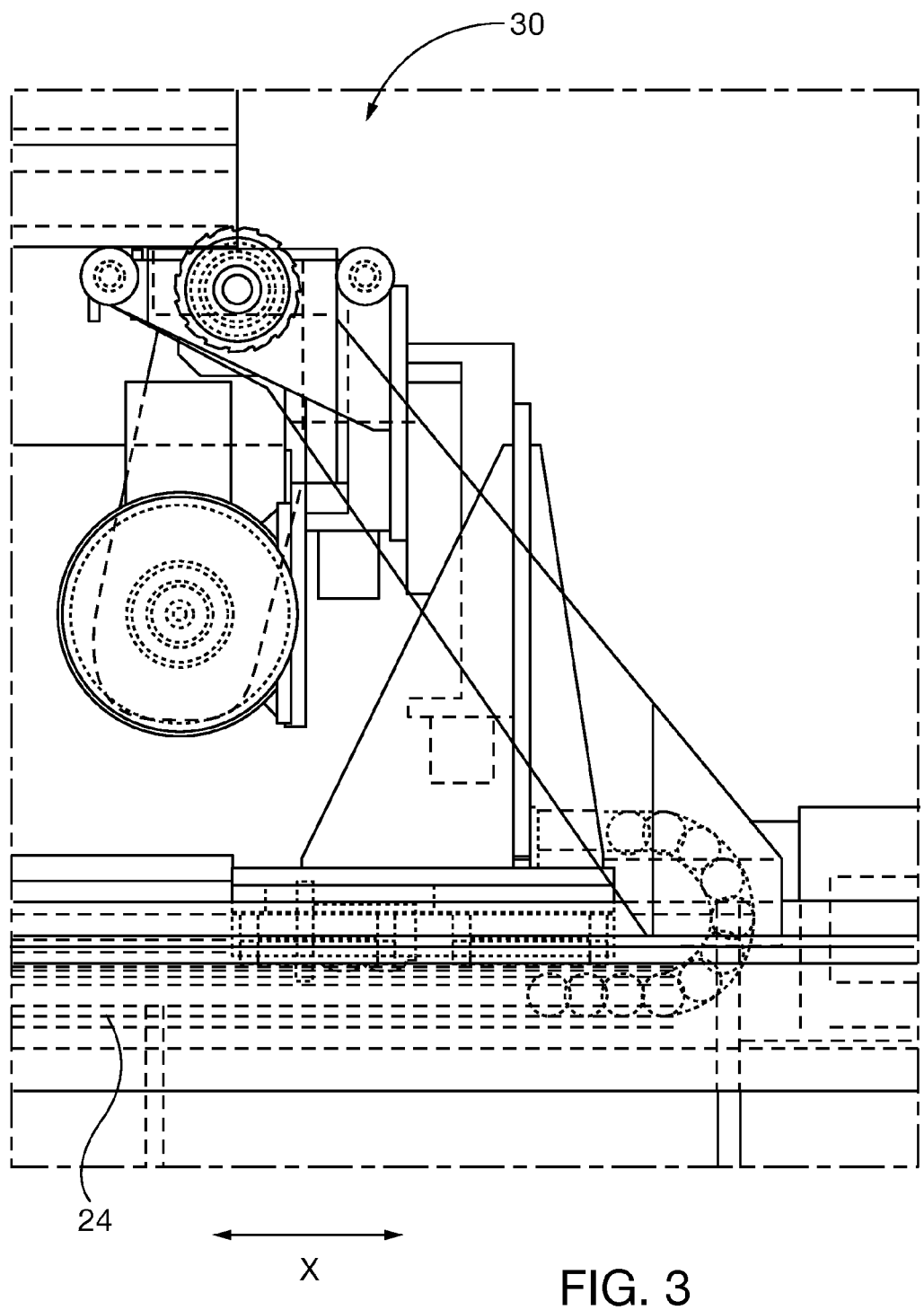
FIG. 3 is a front elevational view of a coil sample cutter, in accordance with an exemplary embodiment of the present invention.
Figure 4:
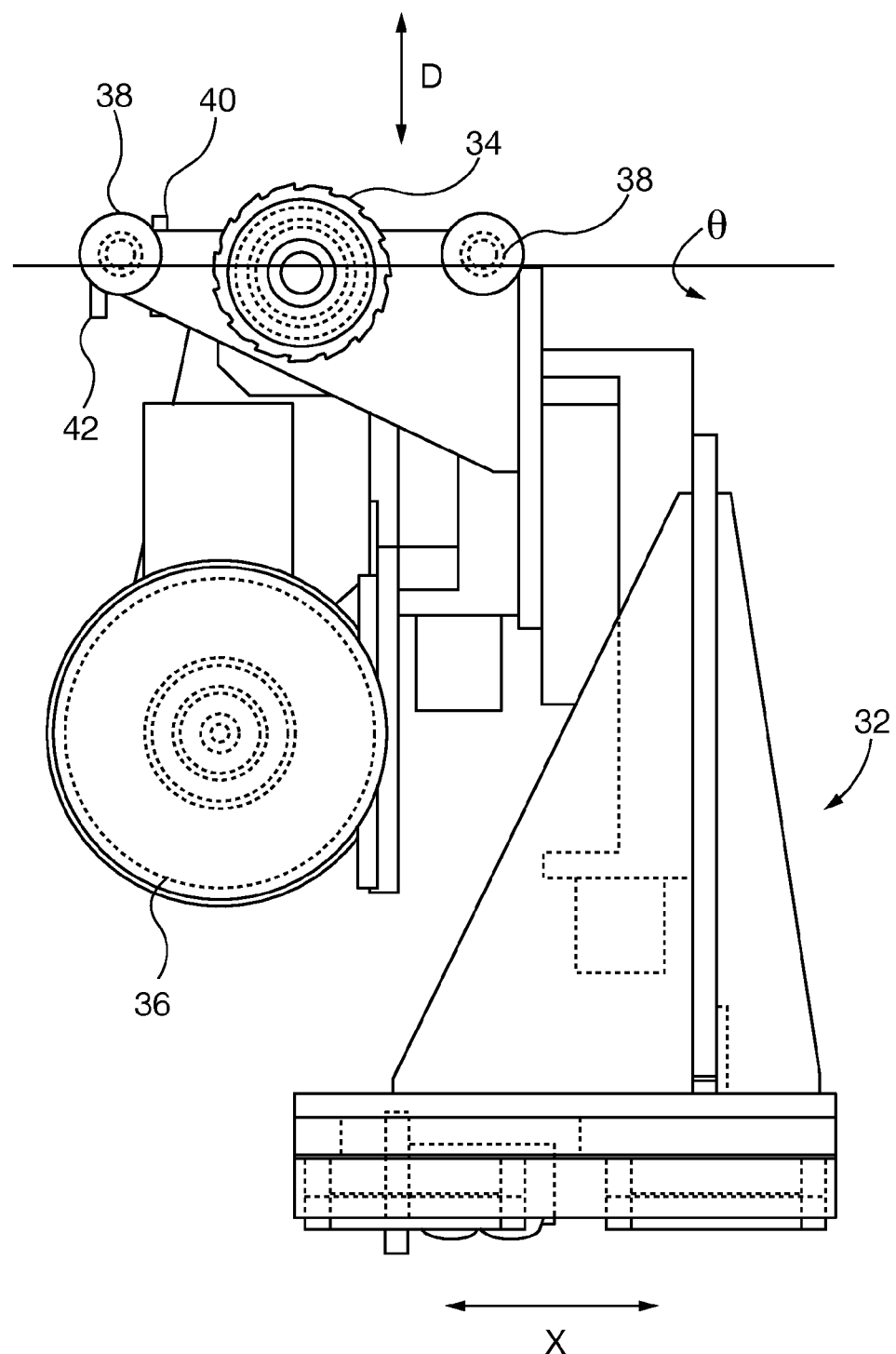
FIG. 4 is a detailed view of FIG. 3, in accordance with an exemplary embodiment of the present invention.

Referring to FIGS. 3 and 4, the sample cutter 30 includes a carriage 32 capable of being radially extended along axis D. The sample cutter 30 has a cutter head 34 that is driven by a motor 36. The sample cutter head 34 is pivoted about the X axis through an angular range of motion θ. A disc-type slot milling tool may be used for the cutter head 34. The cutter head 34 or other cutting tool can have many desired cutting tip profile, including without limitation rectangular, triangular or other pointed tip, radiused-edge rounded lateral ends, arcuate, semi-circular, or oval profiles. Alternative cutting devices may be utilized, such as by way of non-limiting example plasma or electric discharge machining (EDM) heating cutters, broaching cutters or shears. At least one pair of rollers 38 can contact the outer circumferential surface of the coil 10. A proximity sensor 40 can confirm that the sample cutter carriage can be in contact position with the coil 10, and a thickness gauge sensor 42 is adapted to determine the thickness of the coil sheet material at multiple positions across the coil width. Information from a pair of sensors 40, 42 may be communicated to an automated control system for automatic operation of the system, as will be explained in greater detail herein. For example, the automated control system can determine the average material thickness based on the thickness gauge sensor 42 sample readings. As illustrated, the cutter head 34 cuts transversely across the coil sheet web parallel to the coil rotational axis, but one may chose to skew the cut along any desired transverse angle or employ a non-linear cutting path. By cutting between the rollers 22, the coil weight maintains relative pressure between the cutter head 34 and the sheet web, thereby maintaining the web in taut coiled condition.

Figure 5:
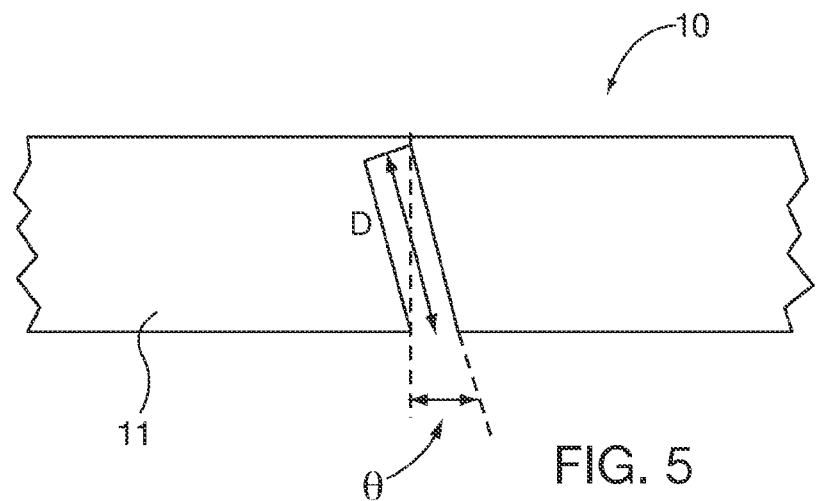
FIG. 5 is a longitudinal sectional view of a coil sheet showing cutting angle and profile made by the coil sample cutter, in accordance with an exemplary embodiment of the present invention.
Figures 7A, 7B:
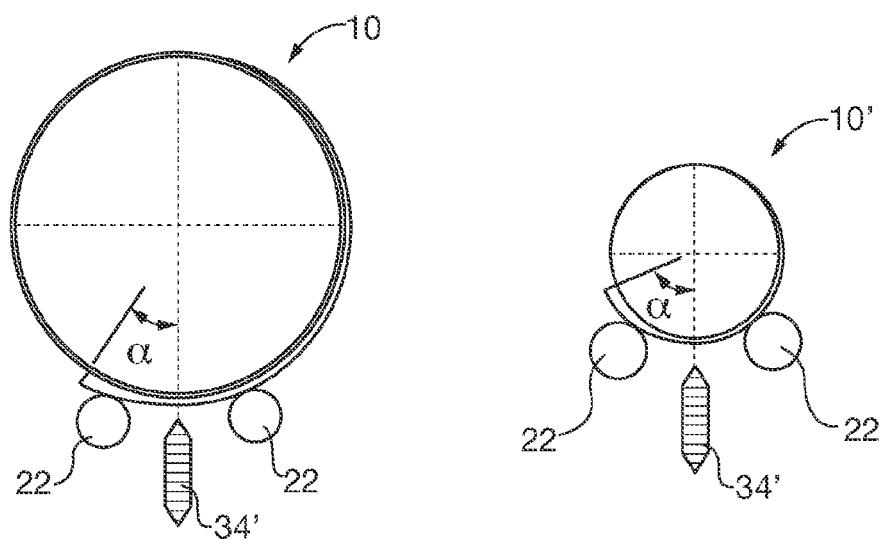
FIGS. 7A. and 7B show exemplary coil rotational positions for two coil diameters, in accordance with an exemplary embodiment of the present invention.

As shown in FIG. 5, the cutter head 34 can be positioned in such a way to create a cut channel of angle θ and radial depth D into the sheet thickness, leaving a thin neck of material at the base of the cut channel. Cut angle θ and depth D are chosen so that the sheet material 11 downstream of the coil may be separated from the main coil 10 without unduly distorting the cut edge remaining on the coil, or leaving a jagged edge. Web material composition, hardness, and thickness may be used as factors for determining cut angle θ and depth D. The partial cut through the sheet thickness can reduce the force necessary to separate the remnant 11 downstream the cut from the rest of the roll after it laterally clears the driven rollers 22, but while the piece remains intact with both sides maintaining the same thickness it is easier to pass them over the rollers. The cut angle θ can be set at zero degrees, orienting the cutting head 34 normal to the coil 10 web. The cut depth D can be chosen to cut all the way through the coil 10 web, so that there is no partial cut. Where no partial cut is desired a cutting head 34', having a triangular or other cross-sectional profile that tapers or otherwise necks to a narrower tip may be utilized, as shown in FIG. 7.

By cutting the coil sheet material at an angle θ greater than zero degrees, cut depth D may be approximated to be slightly less than the web thickness, in order to avoid damaging the web layer underlying the cut zone. In this way tolerance variations in either material web thickness (thinner range of acceptable variation) and/or the cut depth (deeper depth range) will not unduly risk cutting through the entire web and damaging the underlying web layer. Conversely, if the web is at the thicker range of acceptable variation and/or cut depth is in the shallower range, the web neck thickness at the bottom of the cut trough will still be sufficiently thin to facilitate "clean" separation of the sample 11 from the coil 10. Cut angle θ may be generally limited to approximately 30 degrees, with 15 degree cut angle being sufficient for steel sheet of Rockwell C hardness between 17 and 32. Cutting depth D is chosen so that the remaining web neck at the bottom of the cutting trough is less than 0.5 mm (0.020 inches), with 0.35 mm (0.015 inch) being satisfactory for the same hardness range steel. Angle and cutting depth of the trough may be varied for different materials and hardness at the discretion of one skilled in the art.

System General Operation

Referring to FIGS. 6-9, when the coil 10 is positioned between the driven rollers 22, the angular position α of the web end can be determined. The coil 10 is rotated by the rollers 22 so that the web end is a desired number of angular degrees away from the cutting head 34 that corresponds to the desired circumferential, length of the sample to be cut from the coil. Using the example of FIGS. 7A and 7B, if one wishes to cut an approximate 61 cm (~24 inch) sample from an approximate 206 cm (~81 inch) diameter coil 10, the coil can be rotated so that α equals approximately 34 degrees relative to the cutting head 34'. An approximate 107 cm (~42 inch) diameter coil 10', however, can be rotated so that α equals approximately 67 degrees relative to the cutting head 34', to create the same length sample.

Figure 6A:
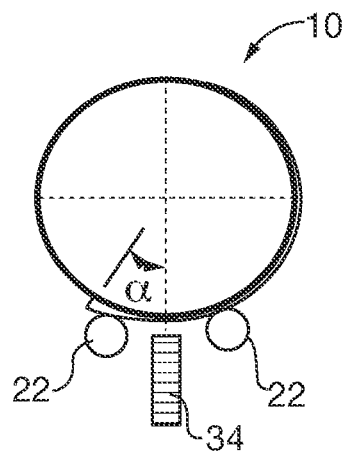
FIGS. 6A-6D is a series of schematic end views showing coil rotational positions during steps of a sampling method, in accordance with an exemplary embodiment of the present invention.
Figure 6B:
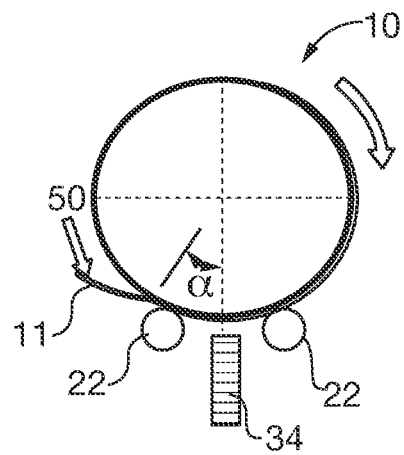
Figure 6C:
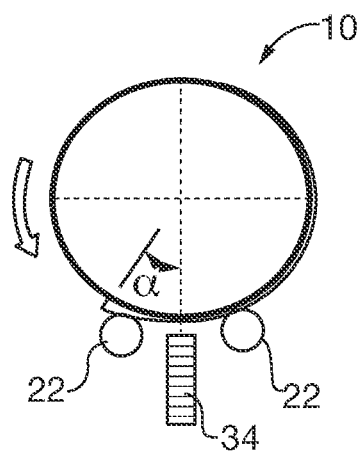
Figure 6D:
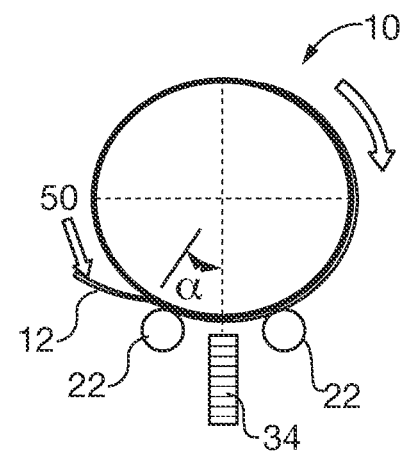

In the exemplary system operational sequence of FIGS. 6A-6D, an approximate 61 cm (~24 inch) long scrap remnant 11 is first cut from the coil 10, and then an approximately 51 cm (~20 inch) long circumferential sample can be cut from the coil. In order to cut the scrap, the approximately 81 inch diameter coil can be initially rotated to align that end is approximately 34 degrees (α) downstream from (i.e., to the left of) the cutter head 34, as shown in FIG. 6A. The cut trough is formed in the web by the cutter head 34, whereupon the coil 10 is rotated clockwise or downstream from the cutter head, so that the cut is laterally clear of its proximal roller 22. In this position the scrap remnant 11 is no longer taut on the coil 10 and relaxes to project generally tangentially from the coil surface. A peeler 50, (for example the robot 50 shown in FIGS. 9 and 10) can shear the scrap generally tangentially relative to the coil 10 surface and breaks the scrap off from the coil along the cut trough narrowed neck.

After the scrap piece is removed, the coil 10 is rotated sufficiently clockwise or counterclockwise, as necessary, to set the desired length of the sample piece remnant 12 (in the present example, approximately 51 cm or ~20 inches) at approximately 32 degrees of angular rotation α relative to the cutter head 34. The next cut trough is created and the coil again rotated clockwise so that the sample piece 12 projects tangentially downstream from the coil outside the proximal roller 22, whereupon peeler 50 separates the sample from the coil. The cut channel created when making the angular cut facilitates smooth passage of the still unitized sheet material (with effectively no discontinuity in thickness) over the driven rollers 22 in either rotational direction. After the sample 12 is removed from the coil 10, it can be rebanded manually while on the sampling system. Alternatively, the unbanded coil 10 can be collected by a coil car and transfer device and banded at a separate station. While in this exemplary operational description a scrap remnant 11 was first cut from the coil 10 prior to cutting a sample remnant 12, one may choose to dispense with the need to remove scrap from the coil 10 end, or alternatively, unspool additional web material from the coil 10 before taking one or more samples. For example, if the coil sample is not on gauge or within tolerance for the gauge required at the proposed cutting position, then a cut can be made and the coil rotated to a new position where the coil is on gauge. The sample can then be taken at this new position.

Figure 8:
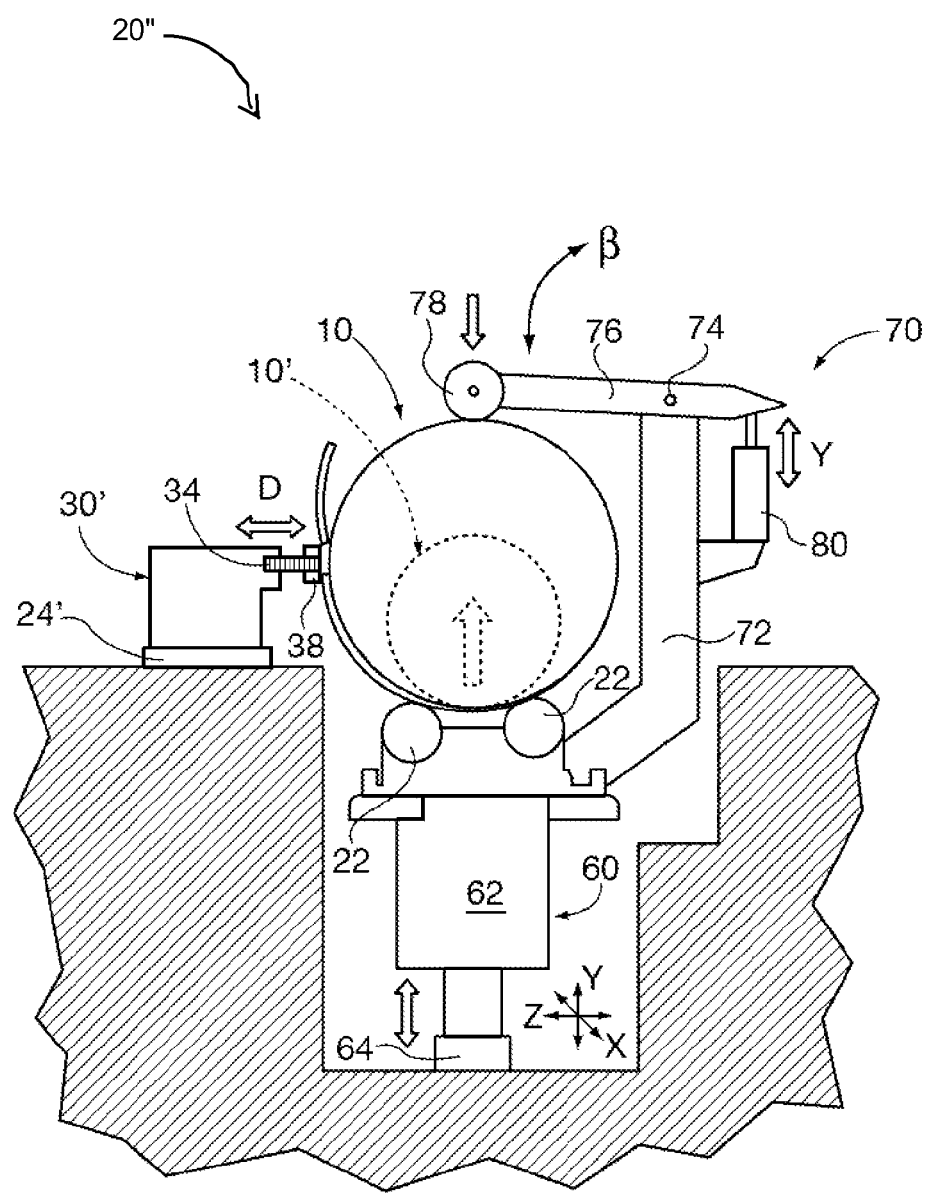
FIG. 8 is a schematic side elevational view of a system loaded with a metal coil, in accordance with another exemplary embodiment of the present invention.

An alternate embodiment sampling system 20' is shown in FIG. 8. In this embodiment the coil 10 can be repositioned vertically in the Y axis dimension by roll alignment lift mechanism 60. The lift mechanism 60 includes a roll support saddle 62 that supports the driven rollers 22. A hydraulic lift 64 can raise and lower the support saddle 62 so that a coil 10 or smaller diameter coil 10' can be positioned relative to cutter 30'. In this embodiment, cutting head 34 is aligned with the radial circumference of coil 10 or 10' at a 9 o'clock relative position rather than at a 6 o'clock position of the previous embodiment of FIGS. 1-7.

The cutter 30' can translate across the X or axial dimension of the coil 10, 10' on linear drive 24'. The cutter 30' is constructed and operates the same as the previously described cutter 30 of the sampling system 20, but as previously noted, aligns the cutting head 34 at the 9 o'clock position rather than at the 6 o'clock position between the rollers 22. The cutter 30' may be aligned radially along the coil 10, 10' circumference at any desired position by repositioning the roll alignment lift mechanism 60 up or down in the Y direction and pivoting the cutting head 34 relative to the coil along angle θ.

A coil tensioner mechanism 70 is adapted to maintain tension on wrapped layers against each other by exerting radially inwardly directed compressive (i.e., squeezing or clamping) tension on the coil 10 or 10'. The coil tensioner 70 inhibits coil relaxation that will otherwise disrupt desired taut tensioning of the coiled web when the web us unwound for cutting. By compressing or squeezing/clamping wrapped coil web layers against each other, web material upstream of the coil tensioner mechanism 70 remains tightly coiled and taut. While a coil tensioner mechanism 70 not shown in the sampling system 20 embodiment, such a mechanism may be used in that embodiment system in order to provide additional coiling tension. The coil tensioner mechanism 70 has a support stanchion 72 is shown coupled to the support saddle 62, so that it moves with a coil 10 supported within the lift mechanism 60. Alternatively, the stanchion 72 does not need to be attached to the lift mechanism 60, and may for example be affixed to the factory floor with its own mechanism to move in coordination with the coil 10 in the Y or vertical dimension. The coil tensioner mechanism 70 includes a boom 76 pivotally coupled to the stanchion 72 by pin 74, so that the boom pivots along an angular path β. Tensioner roller 78 is rotatively coupled to the distal end of the boom 76, and exerts radially inwardly biased compressive force on the coil 10 by actuation of hydraulic cylinder 80, so that the coil 10 is compressed between the rollers 22 and the tensioner roller.

Figure 9:
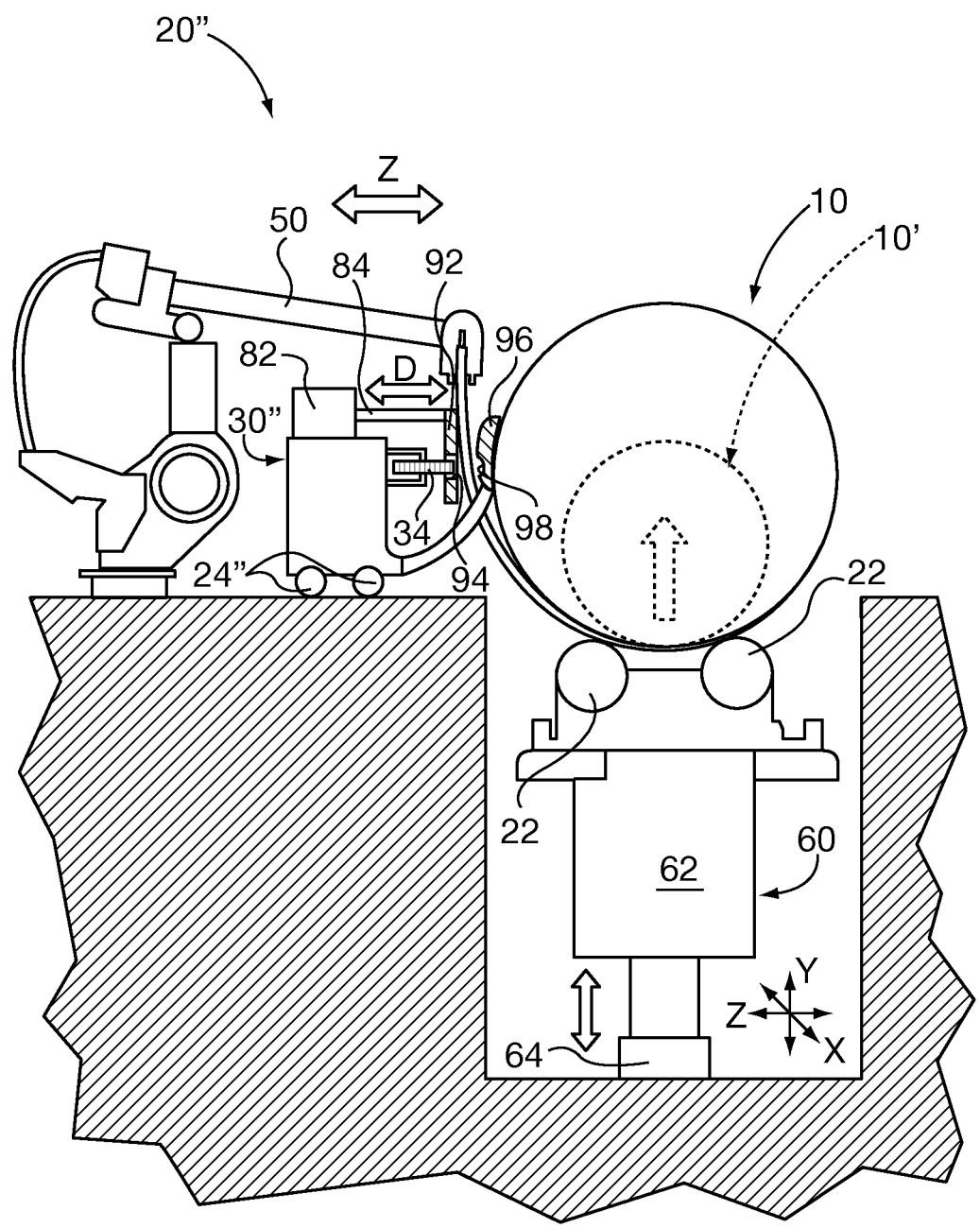
FIG. 9 is a schematic side elevational view of a system loaded with a metal coil, in accordance with an additional exemplary embodiment of the present invention, prior to coil clamping.
Figure 10:
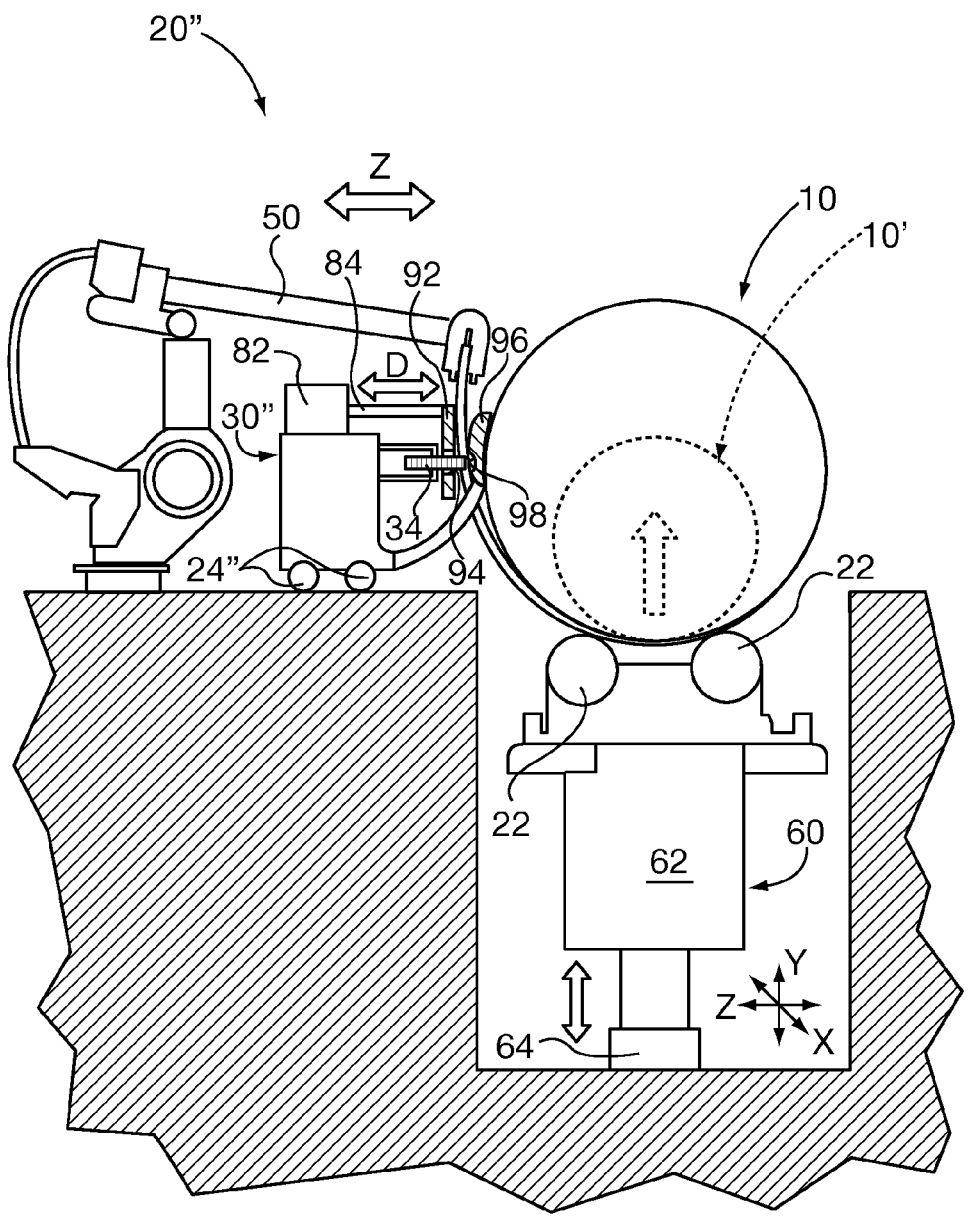
FIG. 10 is a schematic side elevational view of a system loaded with a metal coil, similar to that of FIG. 9, wherein the coil is clamped within the sampling system.
Figure 11:
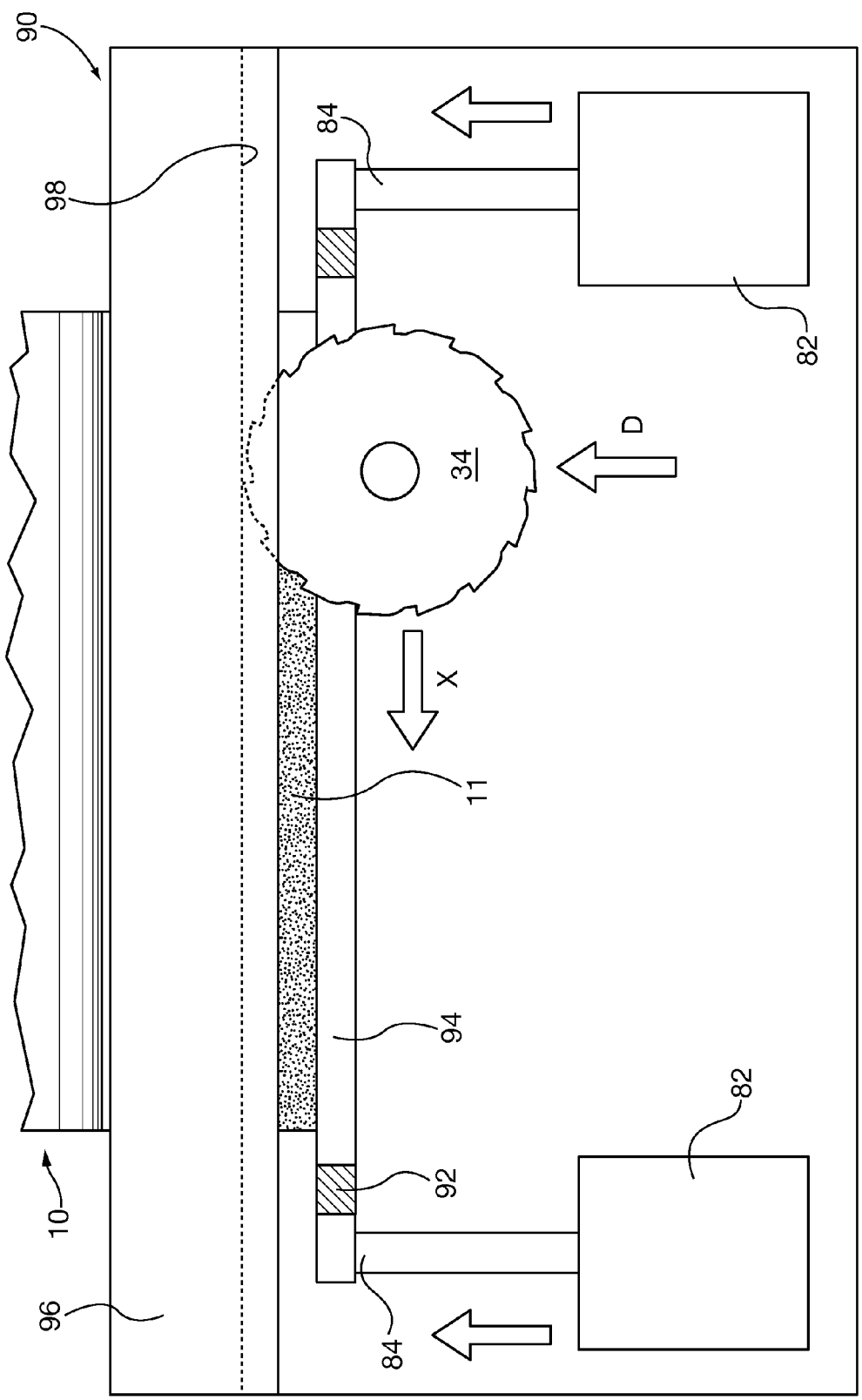
FIG. 11 is a partial cross-sectional plan view of the system of FIG. 10, taken along 11-11 thereof.
Figure 12:
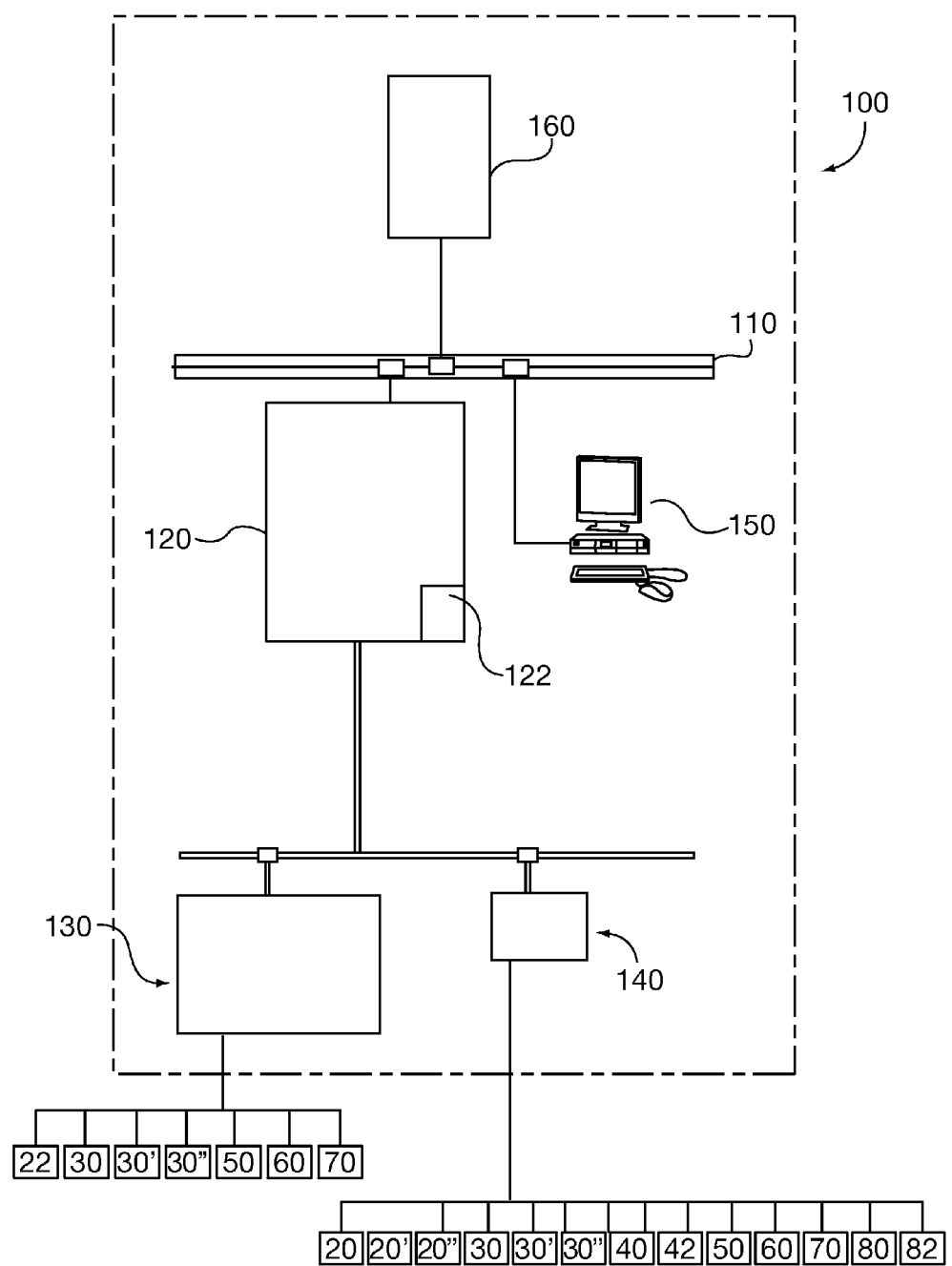
FIG. 12 is a schematic diagram of an automation system for operating the system, in accordance with an exemplary embodiment of the present invention.

FIGS. 9-11 show another embodiment sampling system 20". In this embodiment the cutter 30" is driven on wheels 24" in the Z access direction that is perpendicular to the coil 10 outer circumference. The cutter 30" has a cutter clamp 92, which is an elongated bar spanning across the axial length of the coil 10, having a cutter slot 94 for passage of cutter head 34 therethrough. The cutting head can be driven along a track in the cutter 30" across cutter slot 94 in the X axis to form a traversing cut across the coil 10 outer circumference. Cutter clamp 92 reciprocates in the Z axis direction (toward or away from the coil 10), driven by hydraulic cylinders 82 and piston rods 84 that are coupled thereto. Cutter 30" also has an elongated bar or bumper-like peeler clamp 96 affixed thereto that traverses the coil 10 outer circumference, for abutment against the coil 10 outer circumference as the cutter is translated in the Z access direction. The peeler clamp 96 has a tapered bottom edge to facilitate extension of a scrap end remnant 11 (or sample end remnant 12) thereover and a clearance slot 98 traversing the clamp.

In operation of the sampling system 20" the cutter 30" is abutted to contact against the coil 10, and the cutter clamp 92 is withdrawn in the Z direction away from the coil 10, creating an opening gap between itself and the peeler clamp 96. Next, the coil 10 end remnant (e.g., scrap 11 or sample 12 end) is threaded through that gap by rotating the coil clockwise with the rollers 22, so that the coil end remnant rides over the peeler clamp 96 tapered bottom edge. When a desired length of the coil 10 end extends downstream of the cutter head, e.g., by rotating the coil 10 a desired number of degrees α with the rollers 22, cutter clamp 92 is reciprocated toward peeler clamp 96, effectively squeezing or tensioning the coil end therebetween as a coil tensioner mechanism. Cutter head 34 is advanced into the coil 10 material in the D direction and traversed across a desired axial width of the material in the X axis direction (e.g., across the entire material width in order to facilitate removal of a scrap end 11 sample 12. Cutter head 34 may be advanced or retracted in the D direction by a separate drive axis, or may be manually set by pre-extending it into the cutter clamp 92 cutter slot 94, so that a desired depth cut is formed in the coil 10 material. Cut depth into the coil 10 web material may be selectively set as a partial cut or a full through cut. Notch 98 formed in the peeler clamp 96 allows cutter head 34 clearance if the cutter head is extended beyond the web material through cut depth. Robot 50 is a peeler mechanism to grab the free end of the cut scrap end 11 or sample end 12. If a through cut is performed the robot 50 holds the end 11 or 12 and can transport the end to a desired location. If a partial cut is performed in the end 11 or 12, the robot 50 can be used to snap the remnant end off the web material remaining on coil 10. After cut completion and removal of the end 11 or 12, remaining web material on the coil 10 can be prepared for rebanding by counter rotating the coil in the counterclockwise direction so that the remaining coil free end is proximal or under one of the rollers 22. While not shown, the tensioner mechanism 70 may be used with the sampling system 20" embodiment.

The sampling system embodiments 20, 20', 20" may be incorporated into a fully automated sampling system. Referring to FIG. 9 automated control system 100 includes a communication bus 110 communicatively coupled to a controller having a processor including accessible memory, such as programmable logic controller (PLC) 120 with memory 122. An exemplary bus 110 communication protocol is industrial Ethernet. The memory 122 includes software and/or firmware instruction sets stored therein that when executed by the PLC processor controls operation of system drives 130 and communications cards 140 that are in communication with the system 20, 20', 20" including: its driven rollers, the cutter 30, 30', 30", sensors such as the coil proximity sensor 40 and thickness gauge sensor 42, the sample peeler (e.g., robot) 50, the roll alignment lift 60 and the coil tensioner mechanism 70. Communication and control among the PLC 120, the system drives 130, communication cards 140 and devices coupled thereto is established via a suitable industrial control bus protocol, such as Profibus DP protocol available through the owner of this filed application. The PLC 120 may be in communication via bus 110 with an engineering station 150 for monitoring and altering system operational parameters. A human machine interface (HMI) 160 may also be in communication with the system 100 to enable manual control and monitoring by factory personnel on the shop floor or remote operational station.

Although various embodiments which incorporate the teachings of the present invention have been shown and described in detail herein, those skilled in the art can readily devise many other varied embodiments that still incorporate these teachings.

What is claimed is:

1. A sampling system for extracting a sample from an end strip of a coil having wrapped layers of coiled formed elongated metal, comprising:
    a pair of generally parallel spaced driven rollers, for selective rotation of a coil about a coil central axis that is oriented parallel to the drive rollers;
    a thickness sensing gauge;
    a cutter in communication with the thickness sensing gauge, for selective alignment with a circumference of a metal coil that is oriented parallel to the driven rollers, the cutter having a cutter drive mechanism for selectively aligning and traversing the cutter along a least a portion of the coil end strip, the drive mechanism also advancing the cutter into the coil end strip based at least in part on strip thickness determined by the thickness sensing gauge so as to facilitate a separation of a coil sample from the coil while minimizing material deformation along the separation edge, wherein a cut channel is formed by the cutter having an angle θ relative to the coil central axis and a radial depth D into the strip thickness, leaving a thin neck of material at the base of the cut channel.

2. The system of claim 1 further comprising an automated control system coupled to the driven rollers, the thickness sensing gauge and the cutter drive mechanism for selectively extracting a sample from an end strip of a coil placed on the rollers.

3. The system of claim 2, the automated control system aligning the cutter with the coil end strip based at least in part on coil diameter.

4. The system of claim 3 further comprising a lift mechanism coupled to the automated control system, for selectively varying coil central axis height relative to the cutter.

5. The system of claim 1, the cutter drive mechanism selectively orienting and advancing the cutter so that it is capable of selectively forming a cut channel within an end strip of a coil placed in contact with the driven rollers at a range of angles from zero to less than 90 degrees relative to a coil radius, and a selective range of cut depths up to and including through entire thickness of the end strip.

6. A sampling system for extracting a sample from an end strip of a coil having wrapped layers of coiled formed elongated metal, comprising:
    a pair of generally parallel spaced driven rollers, for selective rotation of a coil about a coil central axis that is oriented parallel to the drive rollers;
    a cutter for selective alignment with a circumference of a metal coil that is oriented parallel to the drive rollers, the cutter capable of selective relative alignment and traverse along a least a portion of the coil end strip, and advancement into the coil end strip so as to facilitate a separation of a coil sample from the coil while minimizing material deformation along the separation edge using a sensor; and
    a coil alignment lift mechanism for selectively varying coil circumferential alignment relative to the cutter, wherein a cut channel is formed by the cutter having an angle θ relative to the coil central axis and a radial depth D into the strip thickness, leaving a thin neck of material at the base of the cut channel.

7. The system of claim 6 further comprising an automated control system coupled to the driven rollers, the coil alignment lift mechanism and the cutter, for selectively extracting a sample from an end strip of a coil placed on the rollers.

8. The system of claim 7, the automated control system aligning the cutter with the coil end strip based at least in part on coil diameter.

9. The system of claim 8, the coil alignment lift mechanism comprising a hydraulic lift and saddle coupled to the driven rollers.

10. The system of claim 6, the coil alignment lift mechanism comprising a hydraulic lift and saddle coupled to the driven rollers.

11. The system of claim 6 further comprising:
    a cutter drive mechanism for selectively aligning and traversing the cutter along a least a portion of the coil end strip and orienting the cutter above the driven rollers; and
    a coil tensioning mechanism abutting the coil circumference proximal the cutter for maintaining tension between coil wrapped layers while cutting a coil sample that is oriented in an upwardly direction above the cutter.

12. The system of claim 11, further comprising a sample peeler for retaining a cut coil sample above the cutter.

13. The system of claim 11, the cutter drive mechanism selectively orienting and advancing the cutter so that it is capable of selectively forming a cut channel within an end strip of a coil placed in contact with the driven rollers at a range of angles from zero to less than 90 degrees relative to a coil radius, and a selective range of cut depths up to and including through entire thickness of the end strip.

14. A sampling system for extracting a sample from an end strip of a coil having wrapped layers of coiled formed elongated metal, comprising:
   a pair of generally parallel spaced driven rollers, for selective rotation of a coil about a coil central axis that is oriented parallel to the drive rollers and extension of a coil end strip;
   a cutter, for selective alignment with a circumference of a metal coil that is oriented parallel to the driven rollers, the cutter having a cutter drive mechanism for selectively aligning and traversing the cutter along a least a portion of the coil end strip for excising a sample therefrom, the drive mechanism also advancing the cutter into the coil end strip so as to facilitate a separation of a coil sample from the coil while minimizing material deformation along the separation edge using a sensor;
   a peeler clamp for retaining the sample during and after excising with the cutter, wherein a cut channel is formed by the cutter having an angle θ relative to the coil central axis and a radial depth D into the strip thickness, leaving a thin neck of material at the base of the cut channel.

15. The system of claim 14, further comprising;
   a cutter carriage coupled to the cutter and peeler clamp, with the carriage selectively translatable in a path generally normal to the coil circumference;
   a cutter clamp proximal to and capable of reciprocation relative to the peeler clamp between an open position that facilitates passage of a coil end there between and a closed position that clamps the coil end there between;
   a cutter clamp drive mechanism selectively reciprocating the cutter clamp, between the open and closed positions; and
   a sample peeler for retaining the coil sample.

16. The system of claim 15, the cutter carriage capable of translation away from the coil circumference while the cutter clamp is in the closed position.

17. A system of claim 14, further comprising:
   the driven rollers extending the coil end strip in an upwardly direction away from the driven rollers;
   the cutter oriented above the driven rollers; and
   the peeler clamp is oriented in an upwardly direction above the cutter.

\* \* \* \* \*